United States Patent [19]

Petrzilka et al.

[11] 4,148,995
[45] Apr. 10, 1979

[54] PROCESS FOR PREPARING CEPHEM LACTONES FOR CEPHALOSPORIN-TYPE ANTIBIOTICS

[75] Inventors: Theodor Petrzilka, Rigistrasse 6, Erlenbach, Switzerland; Gérard Schmid, Lugnorre; Kapa K. Prasad, Basel, both of Switzerland

[73] Assignee: Theodor Petrzilka, Erlenbach, Switzerland

[21] Appl. No.: 816,716

[22] Filed: Jul. 18, 1977

[51] Int. Cl.$^2$ .............................. C07D 501/02
[52] U.S. Cl. ...................... 544/15; 424/246; 260/239 A
[58] Field of Search .................... 544/23, 15

[56] References Cited

U.S. PATENT DOCUMENTS

| 3,708,477 | 1/1973 | Martel et al. | 544/15 |
| 3,905,965 | 9/1975 | Martel et al. | 544/15 |
| 4,016,158 | 4/1977 | Martel et al. | 544/23 |

*Primary Examiner*—Nicholas S. Rizzo

*Attorney, Agent, or Firm*—Werner W. Kleeman

[57] ABSTRACT

Cephem lactones of formula (1)

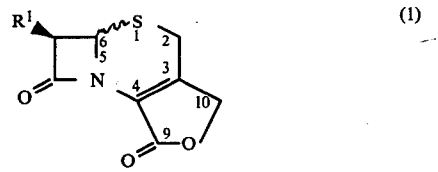

wherein $R^1$ is hydrogen or an organic substituent of the type appearing as the 6-substituent of penicillins or as the 7-substituent of cephalosporins are produced from corresponding 4,5-halohydrin precursors thereof by dehalogenation. Novel stereoisomers of formula (1) compounds as well as novel intermediates for cephem lactone syntheses are disclosed.

The cephem lactones produced according to the invention are of utility as intermediates for cephem-type antibiotics and have antibiotic properties of their own.

17 Claims, No Drawings

PROCESS FOR PREPARING CEPHEM LACTONES FOR CEPHALOSPORIN-TYPE ANTIBIOTICS

BACKGROUND OF THE INVENTION

1. Field of the Invention

The present invention relates to the art of producing synthetic antibiotics and specifically to a process for an improved synthesis of cephem lactones, i.e. a group of compounds known to be of value in the synthesis of cephalosporin-type antibiotics.

2. Description of the Prior Art

Certain cephem lactones have been disclosed in British patent specification No. 948,076 and in the Monography by E. H. Flynn, "Cephalosporins and Penicillins," New York, 1972. A recent review of the state of the art in the field of synthetic antibiotics by P. G. Sammes has been published in Chem. Reviews, 1976, Vol. 76, No. 1, pages 113 to 155. The Sammes review includes, inter alia, a detailed discussion of various syntheses of cephem and cephalosporin type antibiotics and some of the methods involved have become known as Woodward Approach, Roussel-Squibb Route, etc.

It has been recognized for some time that the cephem lactones exhibit antibiotic, or antibacterial, properties, c.f. Journ. Am. Chem. Soc. 84, page 3401 (1962) but, at present, the cephem lactones are of primary importance for production of the corresponding carboxylic acids, i.e. the "classical" antibiotics. For example, the Roussel-Squibb Route, the Beecham Method and the Syntex Approach referred to in the above mentioned review by Sammes include the use of cephem lactones as intermediate components. However, the actual cephem lactone syntheses involved have some severe draw-backs for commercial production as they suffer from one or more of the following disadvantages:

(a) The starting materials used are costly or difficult to produce;
(b) the yields of the target cephem lactones are low;
(c) the end product is racemic.

Thus, it is a main object of the present invention to provide for a cephem lactone synthesis that is improved with regard to one or more of the above noted defects of prior art methods.

Other objects of the invention are novel intermediates suitable for cephem lactone syntheses, and certain novel and valuable stereisomers of such cephem lactones.

Further objects of the invention will become apparent as the specification proceeds.

SUMMARY OF THE INVENTION

It has been found according to this invention that the above objects can be met by a process for producing cephem lactones of the formula (1) — this structure and further structural formulae being shown in the formulae sheet below — wherein $R^1$ is hydrogen or an organic substituent of the type explained in detail below forming the desired cephem lactone structure from a novel precursor compound (formula 4) that corresponds essentially with the target structure of formula (1) without the linking bond between position 4 and has a free or protected hydroxyl in 4-position. Cyclization of this precursor to form the linking 4,5-bond is effected according to the invention by halogenation, preferably by bromination.

A halohydrin or bromohydrin (formula 5) is formed and, after suitably protecting the 4-hydroxyl (formula 6), both the 3-halogen and the protected 4-hydroxyl are removed by dehalogenation, thus forming the 3,4-double bond, i.e. produce the formula (1) cephem lactone.

Preferably, the inventive process includes both the formation of the formula (4) precursor and its conversion into the target cephem lactone (1) by means of a four-step process comprising:

(I) condensing an azetidinone of the formula (2), wherein $R^1$ is as defined above and Y is a leaving group, i.e. a substituent that can be split-off easily in the reaction or condensation, e.g. an acyloxy group, preferably the acetyloxy group, or a sulfonyloxy group, such as a group of formula $HOCH_2(CH_3)_2(O)_2S-$, with a mercaptofuranone of formula (3), wherein either or both the thiol group(s) and the hydroxy may be free (i.e. $R^2$ and/or $R^4$ are hydrogen) or protected (i.e. $R^2$ and/or $R^4$ are protecting groups), e.g. by the tetrahydropyranyl group or an acyl group, such as acetyl. Preferably, the thiol-protecting group, if any, i.e. $R^4$ should be split-off under the conditions of the subsequent reaction step;

(II) the product formed in step (I) is a compound of the formula (4) mentioned above and this compound is reacted with a halogen, e.g. bromine, iodine or chlorine. While fluorine is not preferred, bromine is best suited for most purposes and, thus, is the preferred halogen for step (II). If the protecting group $R^4$ is not removed by the conditions of this halogenation step, it will have to be removed, i.e. converted into hydrogen.

(III) the product of step (II) is the halohydrin of the formula (5) mentioned above. Its 4-hydroxyl is protected now by $R^3$, generally an acyl or sulfonyl and preferably an acyl of from 1–10 carbons, an aryl acyl of preferably 6–18 carbons, an alkyl sulfonyl (alkyl moiety of from 1–10 carbons), an aryl sulfonyl (aryl of from 6–18 carbons), an aryl alkyl sulfonyl or alkaryl sulfonyl (7–18 carbons in both alkyl and aryl). In other words, compound (5) is reacted with an $R^3$-yielding acylating or sulfonating agent explained in more detail below.

(IV) compound (6) obtained in step (III) yields the target or formula (1) compound upon dehalogenation as removal of the 3-halogen will lead to formation of the 3,4-double bond while eliminating $R^3O$ from 4-position.

The symbol $R^1$ appearing not only in the target compound of formula (1) but in the starting azetidinone (2) as well as in the intermediates (4), (5) and (6) may be hydrogen or any of the monovalent organic groups appearing as the 6-substituent of known penicillins or as the 7-substituent of known cephem antibiotics. As long as $R^1$ is hydrogen, the stereochemical orientation of $R^1$ relative to the sulfur atom in 1-position of formulae (1), (5) and (6) is irrelevant. On the other hand, if $R^1$ is an organic group, the corresponding compounds and notably the target compound (1) can be obtained as a mixture of the corresponding cis and trans compounds or recovered as the cis and/or trans isomers from such mixtures. This is indicated in a conventional manner in the formulae where undulated bond lines include either stereomeric configuration, i.e. the cis or trans position of the 1-sulfur relative to $R^1$ (dark wedge-type bonding line used to indicate position above plane of presentation, light wedge-type bonding line indicating position below plane of presentation), and the position of the 3-and 4-substituents in formulae (5) and (6) relative to each other.

It is believed that the easy accessibility of the novel formula (5) compounds vi halogenation, or bromination, respectively, of the formula (4) compounds, i.e. the cyclization-by-halogenation of step (II) in high yields, is surprising and that the improved access to the cephem lactone structure by means of formula (5) compounds is of extraordinary importance for commercial production of cephem-type antibiotics. As mentioned above, the subsequent conversion of formula (5) compounds by first protecting the 4-hydroxy, e.g. by acylation or sulfonation, and subsequent formation of the 3,4-double bond to produce the target compounds (1) does not tend to cause problems.

As mentioned above, $R^1$ may represent a monovalent organic or antibiotics group instead of hydrogen and selection of such a group — while possibly important to the target product — would not normally be critical for the synthesis process if such group is not reactive in the steps of the process, or if a reactive group is protected in a manner obvious to the expert, e.g. so as to avoid an undesired change in the acylation embodiment of step (III) if $R^1$ includes a nitrogen capable of being acylated. The protecting group can be removed after step (IV).

With this explanation in mind, $R^1$ in formula (1) and, hence, in formulae (2), (4), (5) and (6) can be any organic group appearing as the substituent of the 6-position of known penicillins of either natural, semi-synthetic or entirely synthetic provenience, or any organic group appearing as the substituent of the 7-position of known antibiotic cephem derivatives, or cephalosporins, respectively.

Accordingly, the selection of a desired $R^1$ other than hydrogen will be determined primarily by the properties of the final cepham lactones or the derivatives thereof obtainable, for example, by cleavage of the lactone ring, notably in view of the desired pharmacological effectiveness of such compounds for use as antibiotics.

Numerous examples of suitable $R^1$ groups for antibiotic use are given in the above mentioned publications by E. H. Flynn and by P. G. Sammes and both of the said publications are incorporated into this specification by way of reference.

A generally important and preferred class of suitable $R^1$ groups are those of general formula

in which R' and R" are alike or different, and are selected from hydrogen or groups $R^7$, $R^8$, or may — together with the nitrogen of said general formula — constitute a heterocyclic ring or an azomethin group that may or may not carry one or two substituents on the methin carbon.

Preferred specific examples of $R^7R^8$ are those groups bonded directly to the nitrogen of the above general formula or via a carbonyl linkage

thereto and selected from unsubstituted or substituted alkyls or alkenyls having 1–10 carbons in a straight or branched chain, e.g. an α-halo-substituted or β-substituted alkyl having 1–6 carbons, an α-phenyl-β-hydroxyalkyl having 1–5 carbons or an α-substituted phenyl-β-hydroxyethyl radical, where the α-substituent is an alkyl having 1–4 carbons, halogen, trifluoromethyl, alkoxy having 1–4 carbons, nitro, amino or hydroxy; unsubstituted or substituted aryl, arlkaryl or aralkyl, e.g. phenyl, p-dimethylaminophenyl, nitrophenyl, p-carbomethoxyphenyl, p-chlorophenyl, p-ethoxyphenyl, p-methoxyphenyl or naphthyl, an aminoalkyl where the alkyl is an ethyl substituted with phenyl or a straight or branched alkylene having 1–8 carbons, or an N-carbobenzoxy derivative thereof; an α-allylmercaptoalkyl where the alkyl contains 1–6 carbons; cis or trans styrylmercaptomethyl; phenylmercaptomethyl; p-hydroxybenzyl; β-phenylmercapto-β-hydroxyalkyl or α-phenoxy-β-hydroxyalkyl having a 1–7 carbon alkyl or the β-acyl derivatives thereof in which the acyl is derived from a monocarboxylic acid having 1–4 carbons. It should be emphasized that a complete enumeration of all suitable $R^1$ groups is not intended here and that the benzoylamido group mentioned below as $R^1$ is but one of many examples.

Examples of known penicillins, the 6-substituent of which is suitable as $R^1$ for the invention include (P stands for penicillin): benzyl-P, phenoxymethyl-P, Ampicillin, Cloxacillin, Methicillin, Chinacillin, Nafcillin, Ancillin, Carbenicillin, α-sulfamoylphenylacetamido penicillanic acid, α-guanoureidophenylacetamido penicillanic acid, α-carboxy-3-thienylacetamido penicillanic acid, α-amino-4-hydroxyphenylacetamido penicillanic acid, α-aminocyclohexa-1,3-dienylacetamido penicillanic acid, etc.

Examples of cephalosporins, the 7-substituent of which is suitable as $R^1$ for the invention, include Cephalosporin-C, Cephalothin, Cephaloridine, Cephaloram, Cephaloglycin, Cefazoline, Cephapirin, 2,6-dimethoxybenzamido cephalosporanic acid, 3-(o-chlorophenyl)-5-methylisoxazole-4-carboxamido cephalosporanic acid, α-carboxyphenylacetamido cephalosporanic acid, etc.

DESCRIPTION OF PREFERRED EMBODIMENTS

The various steps of the preferred embodiment of the inventive process will now be explained in more detail:

The starting compound (2) of step (I), an azetidinone provided with the required $R^1$ and a suitable leaving group Y can be obtained by methods known per se, cf. H. W. Schnabel et al, Ann. 477 (1974) or German Published Specification DT-OS 1,906,401. Suitable leaving groups, such as acyloxy, e.g. acetyloxy, or sulfonyloxy can be introduced by well known methods. The other starting compound (3) for step (I), i.e. the mercaptofuranone in which either or both the hydroxy and thiol are protected, can also be obtained by methods known per se, e.g. as described by R. Heymès et al, C. R. Acad. Sci. 263, 170 (1966), or in French Patent No. 1,365,959, for the production of 3-hydroxy-4-acetyl-thiomethylfuran-2(5H)-one.

A preferred novel starting compound (3) for step (I) of the inventive process has a free thiol group ($R^4$ is hydrogen) and a hydroxyl that is protected by a group known to be substantially stable under alkaline conditions, e.g. having tetrahydropyranyl as $R^2$. This particular novel mercaptofuranone, i.e. 3-tetrahydropyranyloxy-4-mercapto-methylfuran-2(5H)-one is of outstanding utility for cephem lactone synthesis. Another preferred and novel mercaptofuranone (3) is the 3-tetrahydropyranyloxy-4-acetylthio-methylfuran-2(5H)-one. The structural formula of these novel and preferred formula (3) compounds is given in the formula sheet as formula (12), in which $R^5$ is hydrogen or acyl, e.g. acetyl. In general, those formula (3) compounds are preferred, where $R^2$ is a protecting group (i.e. protecting the hydroxy in the condensation reaction of step (I) while not encumbering the cyclization-by-halogenation in step (II)) and where $R^4$ is hydrogen or a leaving group (i.e. being removed in the condensation reaction of step (I)), e.g. an acyl group of up to 10 and preferably less than 6 carbons such as acetyl.

Condensation of compounds (2) and (3) in step (I) for forming compound (4) preferably is effected at a temperature of about 0° C., e.g. 0° C. ± 10° C., in the presence of an alkali or alkaline substance, e.g. alkali hydroxide such as sodium hydroxide, or a carbonate or hydrogencarbonate of an alkali metal. Organic bases, e.g. tertiary amines, can also be used as alkaline material. Use of a liquid medium for the condensation, e.g. a lower alkanol, is preferred.

Preferably, the product of step (I) is purified prior to its being used in step (II), e.g. by chromatography or the like methods. Further purification by crystallization from a suitable solvent, e.g. methanol, may be effected but is not believed to be essential for the inventive process.

The products of step (I), i.e. the formula (4) compounds, are novel and — aside from their utility as intermediates of interest because they exhibit antibiotic activity.

Step (II) of the preferred process involves cyclization-by-halogenation of compound (4). It is believed that the potentially enolic character of (4) is the reason why halogen, preferably bromine, attacks in the —position so as to form an —haloketone that, in turn, reacts immediately with the imino of the —lactam moiety of (4) to form a mixture of the isomers of the cyclic halohydrins (5).

The halogen can be used in elemental form, preferably as a solution in a liquid that is substantially inert under the reaction conditions, e.g. bromine in a mixture of methanol, dioxane and water (18/2/1). Low temperature halogenation, i.e up to about 0° C. and in the range of about minus 80° C. to 0° is preferred.

The reaction product of step (II) is a mixture of formula (5) isomers which may be separated after purification (e.g. chromatography) of the mixture by fractionated crystallization or the like methods. Such separation, however, is not required for use of the formula (5) compounds in the subsequent step of the inventive process.

The halohydrins of the formula (5) are novel compounds that — aside from their utility as intermediates in cephem syntheses — are of interest because they exhibit antibiotic activity.

Step (III) substantially involves as a preparatory measure for a smooth dehalogenation in subsequent step (IV) the protection of the 4-hydroxy of formula (5) halohydrins, e.g. by conventional acylation or sulfonation. The protecting group $R^3$, e.g. acyl or sulfonyl, can be provided by conventional acylating or sulfonating agents that for the purposes of this specification can be termed $R^3$-yielding agents. Typical examples of such agents are the reative forms of carboxylic and sulfonic acids, e.g. anhydrides or halides of conventional carboxylic acids selective from aliphatic (1-10 carbons), arylic (6-arylaliphatic carbons), alkarylic (6-18 carbons) and arylaiphatic (6-18 carbons) carboxylic acids, and sulfonyl halides, e.g. sulfonyl chlorides derived from alkyl (1-10 carbons), aryl (6-12 carbons), arylalkyl (7-18 carbons) and alkaryl (7-18 carbons).

The particular selection of $R^3$ is not believed to be critical for the subject process as $R^3$ is removed upon dehalogenation in step (IV).

Step (III) yields a mixture of isomers of formula (6) compounds, and these isomers may be separated by conventional methods. Such separation is not required for the purposes of the inventive process.

The formula (6) products of step III are novel. Again, these compounds have utility for cephem syntheses and are of interest because of their antibiotic acitivity.

In step (IV) the formula (1) cephem lactones are produced by dehalogenation of the formula (6) compounds. Upon such removal of the halogen in 3-position the 3,4-double bond that is characteristic of the cephem lactones (1) will be formed directly, i.e. without specific additional process means, as group $R^3O$ in 4-position is removed concommitantly with removal of the 3-halogen.

Suitable dehalogenation methods are known per se in the art. A typical example for such a method is treatment of the formula (6) compounds with a metal, such as zinc, and an acid, such as acetic acid. Generally, any mild reductive treatment can be used for the dehalogenation of step (IV).

Recovering of the formula (1) compound can be effected by conventional means and the product can be purified by chromatography and the like purification means. Also, isolation and recovery of isomers (if $R^1$ is not hydrogen) can be effected by conventional means examples of which have been given above.

Alternatively, either isomer may be produced directly in step (IV) if the halohydrin (5) product is processed for recovery of the isomers after step (II), or if the acylated or sulfonated halohydrins (6) are processed for isomer recovery after step (III), and using either isomer as the starting material of steps (III) or (IV), respectively.

The following non-limiting examples are given to illustrate some preferred embodiments of the invention. For characterization and identification of the compounds the following data definitions are used:

MP: Melting point in °C., uncorrected, Tottoli apparatus with capillaries.

IR: Infrared spectrum taken on Perkin-Elmer Pe 125 and Pe 127; frequencies are in $cm^{-1}$; relative intensities are s (strong), m (medium) and w (weak).

NMR: Nuclear magnetic resonance spectrum taken on Varian HA-100. Chemical displacements are given in ppm relative to standard. Coupling constants J are given in Hertz (Hz); s = singlet, d = doublet, t = triplet, q = quadruplet and b indicates broadened signal. DMSO stands for dimethyl sulfoxide.

MS: Mass spectra taken on Hitachi RMU6-A (ionization energy of 70 eV). Optimum temperatures in °C. are given for each spectrum. hebd.

MA: Microanalytical data are in percent by weight.

RF: Chromagraphic migration coefficient measured on silica-gel plates.

All temperatures are in °C. Percentages are by weight; solvent ratios are by volume. BP stands for boiling point.

EXAMPLE 1

Preparation of
3-Tetrahydropyranyloxy-4-acetylthiomethylfuran-2-(5H)-one (Formula (3), ($R^2$ = tetrahydropyranyl, $R^4$ = acetyl)

6.0 g of 3-hydroxy-4-acetylthiomethylfuran-2(5H)-one (formula 3, $R^2$=H, $R^4$=acetyl) prepared according to Heymes et al, C. R. hebd. Seances Acad. Sc. 263, 170 (1966) were dissolved in 100 ml of methylene chloride. After cooling to 0° C., 10 ml of 3,4-dihydropyran in 40 ml of methylene chloride and a catalytic amount of p-toluene sulfonic acid were added to the solution. After stirring for 3 hours at room temperature, the solution was washed with 50 ml 5% sodium hydroxide solution, dried over sodium sulfate and evaporated to dryness. The residual colorless oil (8.8 g) was chromatographed over "Florisil," a commercial silica-gel for chromatography. By elution with benzene methylene chloride (1:1) 8.1 g (=95% yield) of the compound specified in the title of this example were obtained as colorless oil.

BP 155° C. at $10^{-3}$ Torr; RF in $CHCl_3/CH_3OH$ (95/5) 0.66;
$C_{12}H_{16}O_5S$
calculated: C 52.94, H 5.92, S 11.78
found C 52.98, H 6.10, S 11.59
NMR ($CDCl_3$)
5.84 (s, 1H, OCHO)
4.65 (s, 2H, lactone)
3.87 (s, 2H, $SCH_2$)
3.82–3.50 (m, 2H, $OCH_2THP$)
2.38 (s, 3H, acetyl)
1.88–1.40 (m, 6H, THP)
IR ($CHCl_3$)
2970 (m), 1765 (s), 1440 (m), 1350 (m), 1240 (m), 1120 (m), 1080 (m), 1030 (m), 980 (m), 900 (m), 870 (w)
MS (100° C.)
275 (3), 243 (100), 165 (78), 85 (94), 55 (42).

EXAMPLE 2

Preparation of
3-Tetrahydropyranyloxy-4-thiomethylfuran-2(5H)-one
(Formula (3) $R^2$=tetrahydropyranyl, $R^4$=H)

3.0 g of the product of Example 1 were dissolved in 100 ml of methanol. After cooling of the solution to 0° C. it was saturated with dry ammonia. After 30 minutes the solution was evaporated to dryness. The residue was taken up in 100 ml of benzene and the solution was filtered from the insoluble acet amide. After evaporation of the filtrate the residue, a colorless oil (2.8 g) was purified by chromatography on 30 g of "Florisil." By elution with methylene chloride a total of 2.16 g (85% yield) of the compound specified above was recovered.

RF in $CHCl_3/MeOH$ (95/5) 0.70
IR ($CHCl_3$)
2950 (s), 2885 (m), 1770 (s), 1445 (w), 1380 (w), 1355 (w), 1130 (s), 1080 (s), 1040 (s), 970 (m), 900 (m), 870 (w).
$C_{10}H_{14}O_4S$
calculated: C 52.17, H 6.13, S 13.90
found: C 52.08, H 6.07, S 13.78
NMR ($CDCl_3$)
5.80 (s, 1H, OCHO)
4.86 (s, 2H, $CH_2$ lactone)
3.72 (m, 2H, $OCH_2THP$)
3.51 (d, J=8 Hz, 2H, $SCH_2$)
2.10–1.50 (m, 6H, THP)
1.91 (t, J=8 Hz, 1H, SH exchangeable with $D_2O$)
MS (180° C.)
230 (M+2), 188 (3), 168 (1), 155 (0.8), 146 (3), 112 (8), 85 (100), 83 (55), 69 (12), 67 (8), 66 (10), 55 (78).

EXAMPLE 3

Preparation of
3-Hydroxy-4-(azetidinone-4'-yl)-thiomethylfuran-2-(5H)-one (Formula (4), $R^1$=H, $R^2$=H)

685 mg of 4-acetoxyazetidinone (formula 2, $R^1$=H, V=acetoxy, prepared according to H. W. Schnabel et al, J. Am. Chem. Soc. 477 (1974) and DT-OS No. 1,906,401, respectively) and 1 g of 3-hydroxy-4-acetylthiomethylfuran-2(5H)-one (formula 3, $R^2$=H, $R^4$=acetyl, prepared according to the method by Heymès mentioned in Example 1) were dissolved in 30 ml of methanol. The solution was cooled to 0° C. and a solution of 210 mg sodium hydroxide in 3 ml of water was added. After 30 minutes the mixture was evaporated under vacuum and the residue was subjected to chromatography on a column of 20 g of silica-gel. After removal of non-polar by-products by elution with chloroform, a subsequent elution with ethyl acetate yielded 270 mg of the subject formula (4) compound that was crystallized from methanol. The analytical data of the purifid compound (4) are as follows:

MP 111° C.
RF 50/50 0.60
IR (KBr)
3310 (s), 3010–2960 (w), 1755 (s), 1725 (s), 1665 (s), 1455 (w), 1410 (m), 1360 (m), 1320 (m), 1255 (m), 1236 (m), 1185 (m), 1150 (m), 1130 (s), 1030 (s), 995 (w), 975 (m), 940 (m), 845 (w), 780 (m), 635 (w),
MA
calculated: C 44.66 H 4.22 N 6.51 S 14.90
found: C 44.65 H 4.21 N 6.64 S 14.76
NMR (DMSO)
8,48 (s, b, 1H, OH)
4,79 (2D, 1H, J cis 3Hz, J trans 5 Hz, CHS)
4,76 (s, 2 H, $OCH_2$)
3,64 (s, 2 H, $SCH_2$)
3,34 (2 D, 1 H, J gem 16 Hz, J trans 5 Hz, $CH_2$)
2,75 (2 D, 1 H, J gem 16 Hz, J cis 3 Hz, $CH_2$)
3,50–3,00 (b, 1H, $D_2O$ exchangeable, NH)

EXAMPLE 4

Preparation of the Halohydrins (cis and trans forms of Formula (5), $R^1$=H, Hal=Br)

1.016 g of the compound (4) obtained in Example 3 were dissolved in 20 ml of a mixture of methanol/dioxan/water (17:2:1). The solution was cooled to −70° C. and a solution of 1.5 g of sodium bicarbonate (more than 5 equivalents) were added. A cooled solution (0° C.) of 765 mg of bromine in 1 ml of methanol/water mixture (95:5) was added dropwise to the suspension obtained. The color of bromine disappeared immediately. After completion of the reaction, methylene chloride was added and the mixture was filtered. The filtrate was subjected to chromatography on a column of 20 g of silica-gel. Elution with methylene chloride yielded 976 mg of the bromohydrins (5). The weight ratio of the isomers was 1:1. By fractionated crystallization from methanol the two isomers (5a) (MP 111° C.) and (5b) (MP 147° C.) were recovered from the mixture.

The analytical data of these isomers are as follows:

Isomer (5a)

MP 111° C.
RF 9/1 0.53
IR (KBr)
3449 (m,b), 3200 (m), 1805 (s), 1730 (s), 1635 (w), 1475 (w), 1420 (w), 1360 (m), 1345 (m), 1305 (m), 1285 (m), 1110 (w), 1065 (w), 990 (m),
MA
calculated: C 32,67 H 2,74 N 4,76 S 10.90 Br 27,17
found: C 32,81 H 2,62 N 4,68 S 10.87 Br 27,01
NMR (DMSO)
8,86 (s, b, 1H, OH)
4,67 (ABM g, JAB=2Hz, JBM=5Hz, 1H, CHS)
4,63 (AB g cautered at 4,63, J=9 Hz, CH$_2$O)
3,403 (g, J trans 5 Hz, J gem=14 Hz, CH$_2$CH)
3,44 (s, 2H, CH$_2$S)
2,92 (g. J is=2 Hz, J gem=9 Hz, 1 H CHCH$_2$)
MS (84)
293–295 (M+, Br, 1%), 265,267 (Br, 0,5%), 235,237 (br, 0,5%), 193, 195 (br, 2%), 170 (74%), 128 (100%), 101 (23%), 80,82 (Br, 90%), 44 (97%).

Isomer (5b)

MP 147° C.
RF 9/1 0.47
IR (KBr)
3460 (m), 2975 (w), 1805 (s), 1745 (s), 1470 (w), 1430 (w), 1400 (w), 1340 (s), 1280 (m), 1215 (m), 1180 (s), 1010 (s), 960 (m),
MA
calculated: C 32.67 H 2,74 N 4,76 S 10,90 Br 27,17
found: C 32.63 H 2,83 N 4,85 S 10,95 Br 27,30
NMR
8,20 (s, 1H, OH)
5,19 (d, J=12Hz, 1H, CH$_2$O)
4,87 (g, J cis 2Hz, J trans 5 Hz, 1H, CHS)
4,58 (d, J gem=12 Hz, 1H, CH$_2$O)
3,75 (d, J gem=14 Hz, 1H, CH$_2$S)
3,50 (d, J gem=14 Hz, 1H, CH$_2$S)
3,48 (g, J trans=5 Hz. J gem=15 Hz, CH$_2$CH)
2,88 (g, J cis=2 Hz, J gem=15 Hz, CH$_2$CH)
MS (85° C.)
293,295 (br, M+1%), 265, 267 (br, 0,5%), 235, 237 (br, 0,5%), 193, 195 (br, 2%), 170 (74%), 128 (100%), 101 (23%), 80,82 (br. 90%) 44, (97%).

EXAMPLE 5

Preparation of the Acetylated Halohydrin (Formula (6), $R^1$=H, $R^3$=CH$_3$CO, Hal=Br)

(A) Acetylation of the mixture of isomers: 293 mg of the mixture of the isomers of the bromhydrin (5) were dissolved in 5 ml of dry dimethoxy ethane. A mixture of 116 mg of pyridine and 115 mg of acetyl chloride were added and the reaction mixture obtained was agitated for 15 hours at room temperature. Then, 50 ml of chloroform were added for dilution and the diluted product was washed with diluted aqueous HCl. The residue obtained after evaporation was subjected to chromatography on 5 g of silica-gel. Elution with benzenee yielded a total of 285 mg of the desired acetylated bromhydrin (6). The pyridine may be replaced by triethylamine.

(B) Acetylation of the isomer (5a): 293 mg of the bromhydrin (5a) obtained in Example 4 was acetylated with pyridine and acetylchloride as described in (A). The O-acetylated bromhydrin (6a) was obtained in a yield of about 85% and was crystallized from diethyl ether hexane, (MP 84° C.).

(C) Acetylation of the isomer (5b): 293 mg of the bromhydrin (6b) obtained in Example 4 were acetylated as in (A) above with triethyl amine and acetylchloride to give 302 mg of O-acetylbromhydrin (6b) in a yield of 90%. The product crystallized from methanol melted at 141° C.

The analytical data of (B) and (C) are as follows:

Bromoacetate Isomer (6a)

MP 84° C.
RF 0.68
IR (CHCl$_3$)
3020–2920 (w), 1820 (s), 1785 (s),
1460 (w), 1415 (w), 1370 (m), 1345 (m),
1245 (m), 1390 (m), 1155 (s), 1115 (m),
1080 (m), 920 (m).
MS (200° C.)
355,7 (M+, 0,1%), 265,267 (1%),
196 (55%), 170 (92%), 128 (72%),
80,82 (100%), 44(95%),
NMR (DMSO)
4,85 (d, J=10 Hz, 1 H, OCH$_2$)
4,81 (cf J cis=2 Hz, J trans=5 Hz, 1 H, CHS)
4,70 (d, J=10 Hz, 1 H, OCH$_2$)
3,63 (cf, J trans=5 Hz, J gem=15 Hz, 1 H, CHCH$_2$)
3,55 (s, 2 H, CH$_2$S)
3,18 (cf, J as=z HZ, J gem=15 Hz, 1 H, CHCH$_2$)

Bromoacetate Isomer (6b)

MP 141° C.
RF 9/1 0.6%
I.R. (CHCl$_3$)
(3020–2920)(w), 1820 (s), 1785 (s)
1460 (w), 1415 (w), (1370) (m), 1345 (m)
1245 (m), 1390 (m), (1155) (s), 1115 (m)
1080 (m), 920 (m).
NMR (DMSO)
5,32 (d, J gem=12 Hz,
5,01 (cf, J cis=2 Hz, J trans=5 Hz, 1 H, CHS)
4,62 (d, J gem=12 Hz, 1 H, OCH$_2$)
4,08 (d, J gem=14 Hz, 1 H, CH$_2$S)
3,58 (d, J gem=14 Hz, 1 H, CH$_2$S)
3,54 (cf, J trans=5 Hz, J gem=15 Hz, 1 H, CHCH$_2$)
2,95 (cf, J cis=2 Hz, J gem 15 Hz, 1H, CHCH$_2$)
2,19 (s, 3 H, COCH$_3$)
MS
355,357 (br, M+, 0, 1%), 265,267 (br, 0, 9%)
196 (55%), 170 (92%) 128 (73%)
80,82 (100%), 44 (95%)

EXAMPLE 6

Preparation of Cephem Lactone (Formula (1), $R^1$ =H)

(A) Dehalogenation of the mixed isomers: 335 mg of the mixed isomeric bromoacetates (6) obtained in Example 5(A) were dissolved in 10 ml of acetic acid (90%). The solution was cooled to 0° C. and 1,0 g of zinc powder were added thereto while keeping the mixture at 0° C. The suspension was agitated several minutes and filtered thereafter to remove residual zinc. The filtrate was evaporated under vacuum and the residue obtained was subjected to chromatography on a column of 5 g of silica-gel. The target product (formula (1), $R^1$=H) was obtained in a yield of about 80% by elution of the column with ethyl acetate and crystallized from methanol to yield the pure product, MP 209° C. The analytical data are given below.

(B) Dehalogenation of the individual isomers (6a) and (6b): The bromoacetate (6a) prepared in Example 5(B) was dehalogenated as indicated in Example 6(A) and yielded the same cephem lactone as in Example 6(A) in a yield of 86%. In an analogous manner, the bromoacetate (6b) again yielded the same cephem lactone (formula (1), $R^1=H$) in a yield of 79%.

As the $R^1$ in 7-position of this cephem lactone is hydrogen, there is no difference between cis and trans-forms of this compound.

Cephem Lactone (Formula 1, $R^1=H$)

MP 194° C.
IR (CHCl$_3$)
  2950 (w), 1805 (s), 1775 (m), 1670 (w)
  1420 (w), 1400 (m), 1305 (w), 1300 (m)
  1185 (w), 1155 (m), 1140 (m), 1100 (m)
  1065 (w), 1030 (m), 990 (w),
NMR (DMSO)
  5.02 (s, 2 H, OCH$_2$)
  4.81 (2 D, 1 H, J cis 4 Hz, J trans 6 Hz, CHS)
  3.84 (2 D, 1 H, J gem 16 Hz, J trans 6 Hz, CH$_2$)
  3.76 (s, 2 H, SCH$_2$)
  3.06 (2 D, 1 H, J gem. 16 Hz, J cis 4 Hz, CH$_2$)
MS (<80°)
  197 (M$^+$, 45%), 169 (100%), 155 (55%) 127 (20%), 126 (25%), 99(12% 57 (28%), 45 (40%, 18 (18%).

EXAMPLE 7

Cephem lactone of formula (1) with $R^1=H$ was prepared by the steps in Examples 4 to 6 but starting from the novel compound of formula (12) ($R^5$=acetyl) prepared according to Example 1 and then using this formula (12) compound for condensation with the azetidinone as described in Example 3.

EXAMPLE 8

Example 7 was repeated with the modification that the novel formula (12) compound ($R^5$=H) prepared according to Example 2 was used for the condensation with the azetidinone as described in Example 3.

As the 3-hydroxy of the starting furanone (3) is protected by tetrahydropyranyl as shown in formula (12), a furanone (12) with unprotected mercapto group (i.e. $R^5$ in formula 12=H) can be used and this provides for an improved yield of step (I) of the inventive process.

For this preferred operation, step (I) can be effected as follows:

3.28 g of the product of Example 2 were dissolved in 30 ml of methanol. 1.8 g of the β-lactam acetate (2) were added to the solution and the mixture was cooled to 0° C. A solution of 560 mg of sodium hydroxide in 5 ml of water were added within a period of 30 minutes and the temperature of the mixture was kept at 0° C. for another 15 minutes. The resulting mixture was evaporated. The residue, a yellow oil, was taken up in dioxan and five drops of concentrated hydrochlorid acid were added while cooling. After 30 minutes, the mixture was evaporated and the residue, a colorless oil, was filtered in mixture with ethyl acetate through a column of 30 g of silica-gel. A total of 2.60 g (60% yield) of the formula (4) compound ($R^1=H$, $R^2=H$) were obtained as a colorless oil which was crystallized from methanol to yield a crystalline solid.

The analytical data thereof are as reported in Example 3.

EXAMPLE 9

Preparation of 3-Phenylacetamid-4(2'-hydroxy-1',1'-dimethyl-ethyl-sulfonyl)-2-azetidinone This Example illustrates the preparation of azetidinone (formula (2), $R^1$ is phenylacetamido, Y is —S-(O)$_2$C(CH$_2$)$_2$CH$_2$OH) for use in the inventive process of synthesizing a cephem lactone (formula 1) having as $R^1$-substituent an organic group which is a typical 6-substituent of natural, semi-synthetic or fully synthetic penicillins and a typical 7-substituent of natural, semi-synthetic or fully synthetic cephalosporins.

1.30 g of the K-salt of 6-phenylacetamido penicillanic acid were dissolved in 18 ml of water. After adjusting the pH to 7.0–7.5, the solution was cooled to 0°–5° C. A solution of 0.55 g potassium permanganate in 0.18 ml of 85% phosphoric acid and 14 ml of water was added slowly so that the temperature did not rise above 10° C. The pH of the solution was kept between 6 and 7.7 by adding small amounts of 10% aqueous phosphoric acid or of 5% aqueous sodium hydroxide. Ten minutes after the end of the addition any surplus of potassium permanganate was destroyed by adding sodium bisulfide and the resulting suspension was filtered through a "Celit" filter. 20 ml of ethyl acetate were added to the filtrate. The solution was cooled to 0° C. and the pH then adjusted to 2 by adding 6N hydrochloric acid. The aqueous phase was extracted twice with ethyl acetate and the combined extracts were washed with water and a saturated aqueous NaCl solution.

The organic phase was dried over sodium sulfate and concentrated sufficiently so that upon subsequent dilution with mineral spirit a solid precipitate was formed. This precipitate (1.5 g=90% yield) was crystalline 6-phenylacetamido penicillanic acid sulfone, MP 124° C.

1.72 g of the product thus obtained were dissolved in 12 ml of dry tetrahydrofurane. The solution was cooled to −5° C., whereupon 0.38 ml of pyridine and then 0.62 ml of isobutyl chloroformiate were added. After dilution with ice water, the mixture was extracted three times with methylene chloride. After carefully evaporating the dried methylene chloride solution, 1.47 g (80%) of the corresponding azide (6-substituent is —CON$_3$) were obtained as residue.

The dried residue was dissolved in 60 ml of benzene and the solution refluxed for 20 minutes. Removal of the solvent yielded 1.36 g (79%) of a substantially pure 2,2-dimethyl-1,1-dioxo-6-phenylacetamido-3-penamylisocyanate. A solution of 1.81 g of isocyanate thus obtained in 37 ml of tetrahydrofurane was added dropwise within 3 hours to an agitated solution of 0.5 ml of 1N hydrochlorid acid in 30 ml of water and 30 ml of tetrahydrofurane. The solution obtained was stirred for 40 minutes and then extracted three times with methylene chloride. The extracts were washed with saturated aqueous NaCl, dried over sodium sulfate and the solvent evaporated.

Chromatography of the residue on silica-gel with benzene ethyl acetate (1:1) yielded 1.52 g (90%) of 6-phenylaceto-2,2-dimethyl-1,1-dioxo-3-hydroxy-penam, MP 111°–112° C. (after crystallization from benzene/chloroform).

1.69 g of the penam thus obtained were dissolved in 100 ml of methanol and cooled to 5° C. Then, a solution of 0.095 g of NaBH in 200 ml of methanol/water (1:1), cooled to 5° C., was added. After 2 minutes, the pH was adjusted to 2 by adding 1N hydrochloric acid and 450 ml of saturated aqueous NaCl were added. The mixture was shaken three times with methylene chloride, the organic phase washed with saturated aqueous NaCl, dried over sodium sulfate and evaporated to dryness. The residue obtained (1.60 g, 95% yield) consisted essentially of 3-phenylacetamido-4-(2'-hydroxy-1',1'-dimethylethylsulfonyl)-2-azetidinone and was purified by chromatography on silica-gel and elution with chloroform. The analytical data are as follows:

IR ($CHCl_3$):
3400 (b, NH, OH), 1780 (lactame-CO), 1670 (amide-CO), 1300 (sulfone);

NMR ($CDCl_3$):
7.51 (s, IH, $D_2O$ exchangeable), 7.26 (s, 5H), 7.13 (d, IH, J=10 Hz), $D_2O$ exchangeable 5.78 (dd, IH, $J_1$=4, $J_2$=10 Hz), 5.06 (d, 1H, J=4 Hz), 3.58 (s, 2H), 3.28–3.94 (b, 2H on $D_2O$ exchange collaps into a clean quartet, J=13 Hz, 2H, $CH_2$), 2.10 (b, 1H, $D_2O$ exchangeable), 1.26 (s, 3H, $CH_3$), 1.23 (s, 3H, $CH_3$).

EXAMPLE 10

Preparation of 3-Phenylacetamido-4[4'-thiomethyl-3'-hydroxy-2'-(5'H)-furanon]-2-azetidinone (Formula (4), $R^1$=Phenylacetamido, $R^2$=H)

340 mg of the acetidinone obtained as described in Example 9 and 160 mg of the furanone (formula (12), $R^5$ is H) were dissolved in 10 ml of dry tetrahydrofurane. After adding 10 ml of dry methanol to the solution, 0.139 ml of triethylamine were added. The mixture was agitated for 3 hours at room temperature (20° C.) and then cooled with ice/water. After adjusting the pH with 1N hydrochloric acid to 3–4, 10 ml of saturated aqueous NaCl were added and the mixture was extracted three times with ethyl acetate. The dried liquid was evaporated and the residue subjected to chromatography on silica-gel. The target product of this Example was obtained in this manner as an oil (0.313 g, 90% yield). This product can be used for the halogenation step (II) of the subject process without further purification.

EXAMPLE 11

Preparation of 7-Phenylacetamido-cephem lactone and 6-Epi-7-phenylacetamido-cephem lactone (Formulae (10) and (11), $R^1$= phenylacetamido)

As $R^1$ in the general formula (1) that encompasses these target compounds is an organic group instead of hydrogen, it will be apparent that one of these cephem lactones, e.g. that of formula (10), is the cis isomer (known per se) while the other cephem lactone (formula 11) is a novel trans isomer not obtained by prior art syntheses.

0.348 g of the azetidinone obtained in Example 10 were dissolved in 10 ml of methanol/water/dioxane (91:5:4). The solution was cooled to −65° C. and then added with 0.60 g sodium hydrogen carbonate. Then, 0.178 g of bromine in 1 ml of the solvent mixture just mentioned were added dropwise.

The reaction mixture was evaporated under vacuum and the residue obtained was subjected to chromatography on a silica-gel column. The bromohydrine (formula (5), $R^1$=phenylacetamido) was eluted with chloroform. A total of 0.223 g of the bromohydrine was obtained in this step (II) and used without further purification for step (III) by acetylation at room temperature of the bromohydrine with acetic chloride as the $R^3$-yielding agent in pyridine. Thus, 0.181 g of the bromoacetate (formula (6), $R^1$=phenylacetamido) were recovered upon processing and purification as above.

The bromoacetate thus obtained was dissolved in 10 ml of glacial acetic acid/water (9:1), the solution cooled to 5° C. Then, 0.60 g of zinc powder were added. After 20 minutes, the mixture was filtered, the remaining zinc washed with acetone and the filtrate evaporated under vacuum. The residue obtained was subjected to chromatography on a silica-gel column using ethyl acetate as an elutant. The main fraction obtained (90 mg, 27% yield) was subjected to thick-layer chromatography with ethyl acetate as migrating fluid and the isomers (10) and (11) were obtained separately in this manner.

The formula (10) compound was crystallized from methanol/diethyl ether, MP 210° C.;$[\alpha]_D^{25}$= +142° C. (acetone);

$C_{16}H_{14}O_4N_2S$ 
calculated: C 58.18, H 4.27, N 8.45, S 9.71
found: C 58.07, H 4.29, N 8.31, S 9.67

The formula (10) compound is identical in any analytical method with a sample of 7-amino-cephalosporin lactone obtained by phenacetylation of the authentic compound.

The formula (11) compound was crystallized from methanol/diethyl ether, MP 176°–177° C.,$[\alpha]_D^{25}$= −95° C. (acetone);

IR (DBr): 3370 (NH), 1785, 1745 (β-lactame and lactone-CO), 1670 (amide-CO);

NMR (acetone $d_6$):
8.18 (b, 1H, NH),
7.83 (s, 5H, phenyl),
5.03 (s, 2H, $OCH_2$),
4.91 (dd, 1H, $J_1$=8, $J_2$=2.5 Hz, $H_7$),
4.83 (d, J=2.5 Hz, $H_6$),
3.81 (q,(AB), 2H, J=18 Hz, benzyl, $CH_2$);

$C_{16}H_{14}O_4N_2S$ 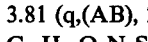
calculated: C 58.18, H 4.27, N 8.48, S 9.71
found: C 58.07, H 4.29, N 8.31, S 9.67.

Unless otherwise specified in the above specification and the appended claims, the term "alkyl" is meant to include straight or branched chain alkyls of from 1 to about 10 carbons including alicyclic monovalent groups and the term "aryl" is meant to include aromatic groups of from about 6 to about 12 carbons. Both the "alkyl" and "aryl" groups may in turn be substituted.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

FORMULAE

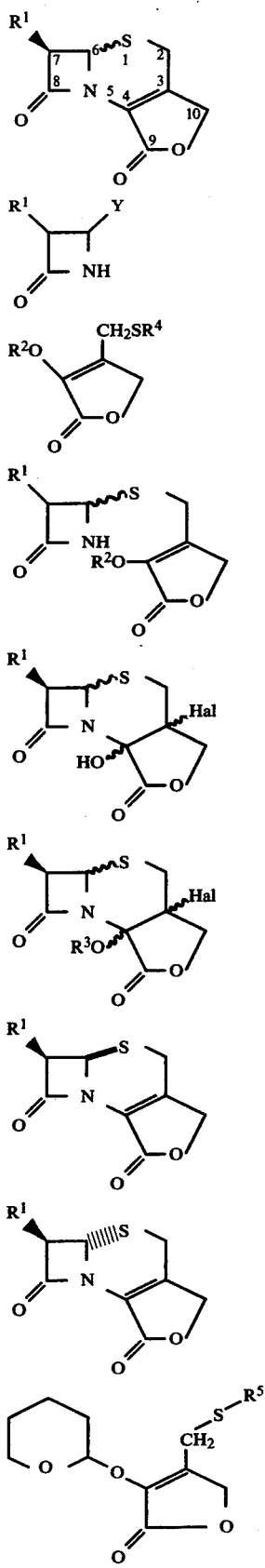

What is claimed is:

1. A process for preparing cephem lactones of the formula (1)

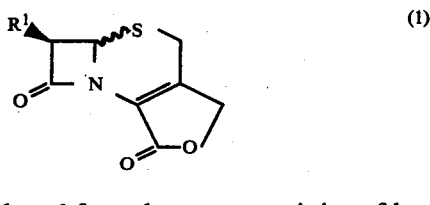

where $R^1$ is selected from the group consisting of hydrogen and organic radicals of the class of the 6-substituents of penicillins and the 7-substituents of cephalosporins; comprising the steps of (1) condensing an azetidinone of the formula (2)

where Y is a leaving group, with a mercapto furanone of the formula (3)

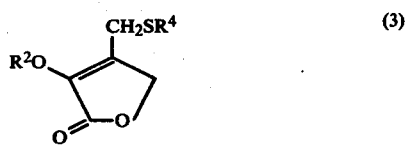

where $R^2$ and $R^4$ are each selected from the group consisting of hydrogen and protecting groups, to form a compound of the formula (4)

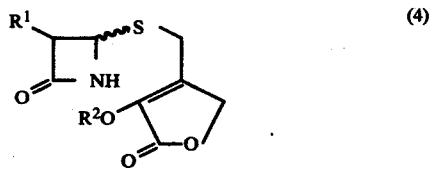

(II) reacting said compound of the formula (4) with a halogen to form a halohydrine of the formula (5)

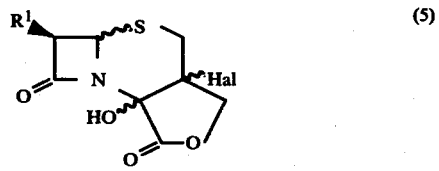

where Hal is a halogen;

(III) reacting said compound of the formula (5) with an $R^3$-yielding agent, wherein $R^3$ is selected from the group consisting of acyl residues including from 1 to about 10 carbon atoms, aracyl residues including from 6 to about 18 carbon atoms, alkylsulfonyl residues in which the alkyl includes from 1 to about 10 carbon atoms; arylsulfonyl residues in which the aryl includes from 6 to about 18 carbon atoms, alkarylsulfonyl residues in which the alkaryl includes from 7 about 18 carbon atoms, and aralkylsulfonyl residues in which the aralkyl includes from 7 to about 18 carbon atoms, to form a compound of the formula(6)

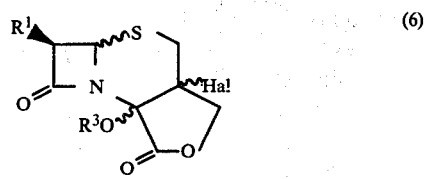

(IV) and removing said halogen and said $R^3O$ from said compound of the formula (6) by dehalogenating to produce said compound of the formula (1).

2. The process of claim 1, wherein said $R^1$ is selected from the group consisting of amino, N-monosubstituted amino and N,N-disubstituted amino.

3. The process of claim 1, wherein said $R^1$ is a substituted amino group of the formula

where R' and R" are selected individually from the group consisting of hydrogen and organic substituents, or where R' and R", together with the nitrogen, form a heterocyclic ring structure or an azomethine group carrying at least one organic group attached to its methine carbon atom.

4. The process of claim 3, wherein one of said R' and R" is hydrogen.

5. The process of claim 1, wherein $R^1$ is selected from the group consisting of phenylacetamido and $C_6H_5CH(NH_2)C(O)NH-$.

6. The process of claim 1, wherein said Y in said compound of the formula (2) is a leaving radical selected from the group consisting of acyloxy and sulfonyl radicals capable of being split-off upon condensation with said compound of the formula (3).

7. The process of claim 1, wherein said Y in said compound of the formula (2) is selected from the group consisting of acetoxy and $-S(O)_2C(CH_3)_2CH_2OH$.

8. The process of claim 1, wherein said radical $R^2$ in said compound of the formula (3) is the tetrahydropyranyl radical.

9. The process of claim 1, wherein said radical $R^4$ in said compound of the formula (3) is an acyl group containing up to about 10 carbon atoms.

10. The process of claim 1, wherein said compound of the formula (4) is reacted in said step (II) with bromine to form the bromohydrine of the formula (5).

11. The process of claim 1, wherein said $R^3$-yielding agent in said step (III) is selected from the group consisting of the acylating and sulfonating agents.

12. The process of claim 1, wherein said compound of the formula (6) is dehalogenated in said step (IV) by a reductive reaction with a metal and an organic acid.

13. The process of claim 12, wherein said metal is zinc and said organic acid is acetic acid.

14. The process of claim 1 comprising an additional step of separating the mixture of stereoisomers of the formula (1) for isolating at least one stereoisomer selected from the group consisting of stereoisomers of formulae (1a) and (1b)

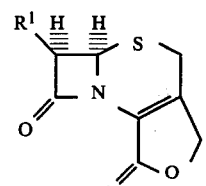

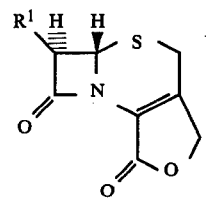

15. A process for preparing cephem lactones of the formula (1)

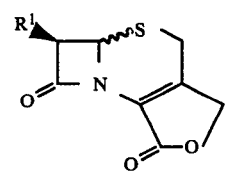

where $R^1$ is selected from the group consisting of hydrogen and organic radicals of the class of the 6-substituents of penicillins and the 7-substituents of cephalosporins; comprising reacting a compound of the formula (4)

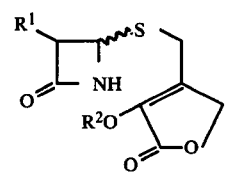

where $R^2$ is selected from the group consisting of hydrogen and protecting groups, with a halogen to form a compound of the formula (5)

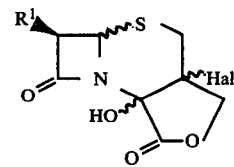

where Hal is halogen, and converting said compound of the formula (5) into said cephem lactone of the formula (1) by removal of said halogen and thereby forming the 3,4-double bond.

16. The process of claim 3, wherein at least one of said R' and R" has the formula

where $R^8$ is an unsubstituted or substituted alkyl or alkenyl havng 1-10 carbons in a straight or branched chain taken from the group consisting of α-halo-substituted or β-substituted alkyl having 1-6 carbons, α-phenyl-β-hydroxyalkyl having 1-5 carbons, α-substituted phenyl-β-hydroxyethyl radical, where the α-substituent is alkyl having 1-4 carbons, halogen, trifluoromethyl, alkoxy having 1-4 carbons, nitro, amino or hydroxy.

17. The process of claim 3, wherein at least one of said R' and R" has the formula

where R⁸ is an unsubstituted or substituted aryl, alkaryl or aralkyl, taken from the group consisting of phenyl, p-dimethylaminophenyl, nitrophenyl, p-carbomethoxyphenyl, p-chlorophenyl, p-ethoxyphenyl, p-methoxyphenyl or naphthyl, an aminoalkyl where the alkyl is an ethyl substituted with phenyl or a straight or branched alkylene having 1-8 carbons, N-carbobenzoxy derivative thereof; α-allylmercaptoalkyl where the alkyl contains 1-6 carbons; cis or trans styrylmercaptomethyl; phenylmercaptomethyl; p-hydroxybenzyl; α-phenylmercapto-β-hydroxyalkyl or α-phenoxy-β-hydroxyalkyl having a 1-7 carbn alkyl or the β-acyl derivatives thereof in which the acyl is derived fom a monocarboxylic acid having 1-4 carbons.

* * * * *